United States Patent [19]

Heyman

[11] 4,117,731
[45] Oct. 3, 1978

[54] PSEUDO CONTINUOUS WAVE INSTRUMENT

[75] Inventor: Joseph S. Heyman, Gloucester, Va.

[73] Assignee: The United States of America as represented by the Administrator of the National Aeronautics and Space Administration, Washington, D.C.

[21] Appl. No.: 858,763

[22] Filed: Dec. 8, 1977

[51] Int. Cl.² .................................... G01N 29/00
[52] U.S. Cl. ................................. 73/579; 73/589
[58] Field of Search ............... 73/579, 659, 580, 581, 73/582, 583, 599, 88 F, 589

[56] References Cited

U.S. PATENT DOCUMENTS

| 3,345,862 | 10/1967 | Rowe | 73/579 |
| 4,014,208 | 3/1977 | Moore et al. | 73/88 F X |

*Primary Examiner*—Jerry W. Myracle
*Attorney, Agent, or Firm*—William H. King; Howard J. Osborn; John R. Manning

[57] ABSTRACT

A device for measuring acoustic properties and their changes in a sample of liquid, gas, plasma or solid. A variable frequency source is applied to the sample by means of a transducer to produce sound waves within the sample. The application of the variable frequency source to the sample is periodically interrupted for a short duration. Means are connected to the transducer for receiving the resulting acoustic signals during the interruptions for producing a control signal indicative of a difference in the frequency of the output of the variable frequency source and the frequency of a mechanical resonant peak in the sample. The control signal is applied to the variable frequency source to maintain its output frequency at the frequency of the mechanical resonant peak. The change in frequency of the variable frequency source is indicative of the shift in frequency of the mechanical resonant peak and the amplitude of the acoustic signals is indicative of the attenuation of the acoustic signals in the sample.

10 Claims, 2 Drawing Figures

PSEUDO CONTINUOUS WAVE INSTRUMENT

ORIGIN OF THE INVENTION

The invention described herein was made by an employee of the United States Government and may be manufactured and used by or for the Government for governmental purposes without the payment of any royalties thereon or therefore.

BACKGROUND OF THE INVENTION

This invention relates generally to ultrasonics and more specifically concerns the measurement of acoustic properties and their changes in liquids, gases and solids.

The two general classes of prior art ultrasonic measuring devices are pulse echo devices and continuous wave (CW) devices. The disadvantages of the pulse echo devices are the acoustic waves are nonmonochromatic and noncoherent, the measurements suffer from broadband and duty cycle effects and the devices usually require very fast rise time electronics and high peak powers leading to instrumentation complexity and expense.

The primary disadvantage of CW devices is "crosstalk" (electrical leakage) which complicates measurement interpretation. This problem requires care to isolate the receiving transducer from the transmitting transducer to minimize the cross-talk. A partial solution to this problem requires a complex transducer having high acoustic coupling yet high electrical isolation. Such a complex transducer is expensive and fragile.

A sampled continuous wave (SCW) device disclosed in a paper entitled A "Sampled-Continuous Wave" Ultrasonic Technique and Spectrometer by J. G. Miller and D. I. Bolef published in The Review of Scientific Instruments, Vol. 40, No. 7, pages 915-920, July 1969, gates off the CW source and waits for the acoustic decay sampling as desired. This comes close to a CW ultrasonic measuring device with no cross-talk; however, it has the disadvantage that it is duty cycle bound. That is, the ratio of signal time to time for a complete cycle is low.

It is, therefore, a primary object of this invention to provide an ultrasonic measuring instrument that has no cross-talk.

Another object of this invention is to provide an ultrasonic measuring device that has nearly one-hundred percent duty cycle.

A further object of this invention is to provide an ultrasonic measuring device that requires only a very simple transducer.

Still another object of this invention is to provide a simple, inexpensive, portable, yet accurate means for measuring acoustic properties and their changes in liquid, gases, plasmas and solids.

Other objects and advantages of this invention will become apparent hereinafter in the specification and drawings.

SUMMARY OF THE INVENTION

A voltage controlled oscillator (VCO) controlled by an FM signal has its output applied through a transducer to the sample whose acoustic properties are to be measured. Several times during each cycle of the FM signal the output from the VCO to the transducer is interrupted momentarily. During these interruptions the resulting CW acoustic waves set up in the sample are detected. The detected CW acoustic waves are combined to form a CW signal that has a DC component and an FM component having the same frequency as the FM signal. The detected CW signal is in phase with the FM signal if the output of the VCO is at a frequency that is on the rising slope of the frequency response curve of a mechanical resonant peak of the sample; and the detected CW signal is out of phase with the FM signal if the output of the VCO is at a frequency that is on the downward slope of the frequency response curve of the mechanical resonant peak. The phase of the CW signal is compared with the phase of the FM signal and if the two signals are in phase a positive DC voltage is integrated by an integrator and then added to the FM signal before it is applied to the VCO. If the two signals are out of phase a negative DC voltage is applied to the integrator and added to the FM signal to lower the DC level of the output of the integrator before it is applied to the VCO. Consequently, the frequency of the VCO is held approximately at the frequency of the mechanical resonant peak. The frequency change of the VCO is indicative of the shift of the frequency of the mechanical resonant peak and is measured by measuring the output frequency of the VCO or by measuring the DC level of the voltage at the output of the integrator. The attenuation of the sample is determined by measuring the DC level of the CW signal just after it is detected, sampled and held.

DETAILED DESCRIPTION OF THE INVENTION

Figure 1:
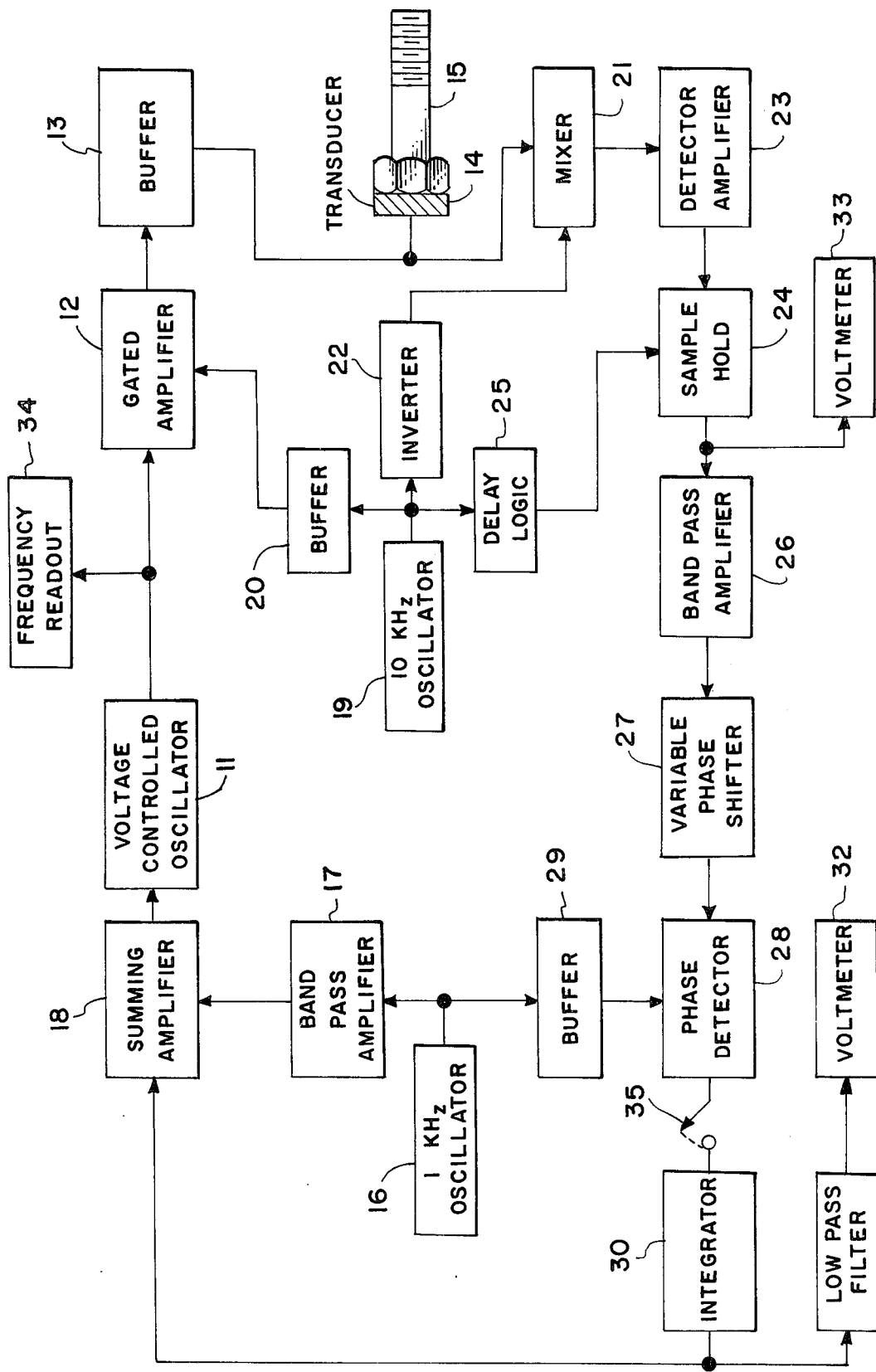
FIG. 1 is a block diagram of the embodiment of the invention selected for illustration in the drawings.

Turning now to the embodiment of the invention selected for illustration in the drawings the number 11 in FIG. 1 designates a varactor tuned voltage controlled oscillator (VCO) which provides an initial radio frequency of for example, $5 \times 10^6$ Hz. The output of the VCO is highly amplified in a gated amplifier 12 which has an on to off gain ratio greater than 70 dB. The output of the gated amplifier 12 is buffered by a buffer 13 to drive a low impedance and then fed to a transducer 14 which converts the electrical radio frequency signals to acoustic waves which are introduced into a bolt 15. Even though bolt 15 is shown in FIG. 1, it is to be understood that this invention is operable on any sample of liquids, gases, plasmas or solids. VCO 11 is frequency modulated by a 1 KHz oscillator 16 whose square wave output is converted to a sine wave by means of a bandpass amplifier 17 and then applied through a summing amplifier 18 to VCO 11.

The output from a 10 KHz oscillator 19 is applied through a buffer 20 to gated amplifier 12 to gate amplifier 12 off for a brief period, for example, 10 microseconds each cycle of oscillator 19. During the times that amplifier 12 is gated off some of the acoustic energy in sample 15 is converted back to electrical signals by transducer 14 and passes through a mixer 21. The output from oscillator 19 is also applied through an inverter 22 to mixer 21 only while gated amplifier 12 is gated off. The signals passed through mixer 21 are detected and amplified by a detector amplifier 23 and then applied to a sample hold circuit 24. The output of oscillator 19 is also applied through a delay logic 25 to ensure that the signals are not sampled during transients after gated amplifier 12 is gated off. Each signal sampled by the sample hold circuit 24 is held until the next signal is sampled. The output of sample hold circuit 24 is applied through a bandpass amplifier 26 resulting in a sine wave on a DC voltage. This signal is applied through a variable phase shifter 27 to a phase detector 28.

The output of oscillator 16 is applied through a buffer 29 to phase detector 28. If the phase of the signal at the output of variable phase shifter 27 is in phase with the signal at the output of buffer 29 then phase detector 28 applies a positive DC voltage through a switch 35 to an integrator 20 which integrates the DC voltage. If the two signals are out of phase, phase detector 28 applies a negative DC voltage to integrator 30. Consequently, integrator 30 produces a DC voltage level that is constantly varying. The DC voltage level is a pseudo continuous wave (PCW). This DC voltage is added to the output from amplifier 17 by means of summing amplifier 18 and then applied to VCO 11. The output of integrator 30 is also passed through a low pass filter 31 and then measured by a DC voltmeter 32 to give an indication of the frequency shifts of a mechanical resonant peak of sample bolt 15. The output of sample hold circuit 24 is measured by a DC voltmeter 33 to give an indication of the attenuation of bolt 15. The frequency shifts of the mechanical resonant peak can also be measured by use of a frequency readout 34 connected to the output of VCO 11.

Figure 2:
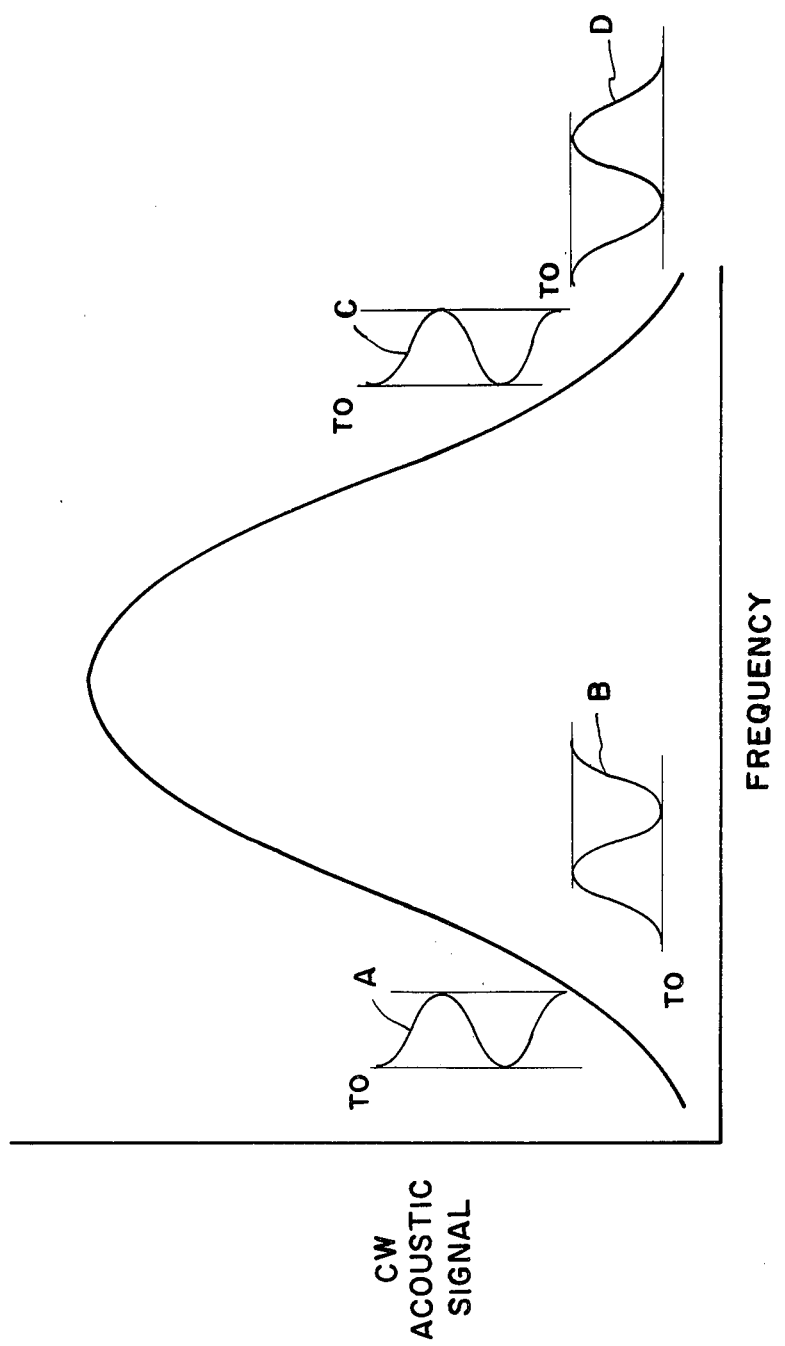
FIG. 2 shows a mechanical resonance response curve for the purpose of explaining how the invention operates.

In the operation of this invention, with the sample bolt 15 being untightened and no strain on it the system is put into operation and the variable phase shifter 27 is adjusted to give maximum reading on voltmeter 33. This ensures that the output frequency of VCO 11 is equal to the frequency of a mechanical resonant peak for the sample bolt 15. Switch 35 is then closed thus locking the PCW to a bolt resonance. Thereafter when the sample bolt 15 is tightened and a strain is put on it the frequency of the mechanical resonant peak will shift. If the shift is such that the sine wave at the output of bandpass amplifier 17 is on the rising slope of the frequency response curve as shown by curve "A" in FIG. 2, then the sine wave generated at the output of variable phase shifter 27 is shown by curve "B". As can be noted, curve "B" is in phase with curve "A". Hense phase detector 28 will apply a positive DC voltage to integrator 30 which will increase the DC voltage at the output of integrator 30. This increase in the DC voltage applied to VCO 11 increases the frequency of the output of VCO 11 such that its frequency approaches the frequency of the peak of the frequency response curve. Conversely, when the sine wave at the output of bandpass amplifier 17 is operating on the down slope of the mechanical resonant peak of sample bolt 15 as shown by curve "C" in FIG. 2, the sine wave produced at the output of variable phase shifter 27 is shown by curve "D". It will be noted that curve "D" is 180° out of phase with curve "C". Hence, phase detector 17 will apply a negative DC voltage to integrator 30 which will decrease the DC voltage level at the output of integrator 30. This decrease in DC voltage applied to VCO 11 decreases its output frequency in the direction of the frequency of the peak of the frequency response curve. Hence, the output of VCO 11 will always be approximately at a frequency corresponding to the frequency of the mechanical resonant peak of sample bolt 15. The shift in frequency as measured by voltmeter 32 or frequency readout 34 is indicative of the strain on bolt 15.

All of the electrical components disclosed in FIG. 1 are old and wellknown and are commercially available. Hence, the details of these components are not disclosed in this application.

The advantages of the present invention over prior ultrasonic measuring devices are numerous. It does not suffer from being a broadband measurement containing many frequencies and phases as do pulse echo devices. It does not have cross-talk as do most CW devices. It is not duty cycle bound as is the previously mentioned SCW and it has a higher signal-to-noise ratio than the SCW since it samples the signal more frequently.

The advantages of the present invention over the SCW are due primarily to the fact that in the SCW the acoustic response in the sample has to build up from zero each time the transmitter is turned on. Whereas, in the present invention the acoustic response falls only slightly below CW equilibrium each time the transmitter is turned off.

What is claimed as new and desired to be secured by Letters Patent of the United States is:

1. A device for measuring the acoustic properties and their changes in a sample comprising:
  a variable frequency source;
  transducer means for applying the output of said variable frequency source to said sample;
  means for periodically interrupting the application of said variable frequency source to said sample for a short duration;
  means connected to said transducer means for receiving the resulting acoustic signals during said interruptions for producing a control signal indicative of a difference in the frequency of the output of said variable frequency source and the frequency of a mechanical resonant peak of said sample; and
  means for applying said control signal to said variable frequency source to maintain the frequency of the output of said variable frequency source at the frequency of said mechanical resonant peak.

2. A device for measuring the acoustic properties and their changes according to claim 1 wherein said variable frequency source is a voltage controlled oscillator.

3. A device for measuring the acoustic properties and their changes according to claim 1 including means for measuring the change in frequency of said variable frequency source thereby giving an indication of the shift in frequency of said mechanical resonant peak.

4. A device for measuring the acoustic properties and their changes according to claim 1 including means for measuring the amplitude of said control signal thereby giving an indication of the shift in frequency of said mechanical resonant peak.

5. A device for measuring the acoustic properties and their changes according to claim 1 including means for measuring the amplitude of said acoustic signals thereby giving an indication of the attenuation of the acoustic signals in said sample.

6. A device for measuring the acoustic properties and their changes according to claim 1 wherein said means for producing a control signal comprises:
  an FM signal, having a frequency several times less than the frequency of said interruptions, applied to the input of said variable frequency source to control its output frequency;
  means for detecting said acoustic signals during each of said interruptions;

means for sampling and holding each of said detected signals to form a CW signal having a frequency equal to the frequency of said FM signal;

means for comparing the phase of said CW signal with said FM signal and producing a positive DC voltage when the two signals are in phase and for producing a negative DC voltage when the two signals are out of phase; and means for adding the produced DC voltage to said FM signal to form said control signal.

7. A device for measuring the acoustic properties and their changes according to claim 6 wherein said produced DC voltage is integrated before it is added to said FM signal.

8. A device for measuring the acoustic properties and their changes in a sample comprising:

a voltage controlled oscillator;

an FM signal for controlling said voltage controlled oscillator;

transducer means for applying the output of said voltage controlled oscillator to said sample;

means for interrupting the application of the output of the said voltage controlled oscillator to said sample several times during each cycle of said FM signal;

means for detecting the amplitude of said acoustic signals in said sample during each of said interruptions and for forming a CW signal therefrom;

means for comparing the phase of said CW signal with the phase of said FM signal and for producing a negative DC voltage when there is a difference in phase and for producing a positive DC voltage when the DC signal is in phase with the FM signal; and means for adding said DC signal to said FM signal before it is applied to said voltage controlled oscillator whereby the output frequency of said voltage controlled oscillator is maintained at the frequency of a mechanical resonant peak of said sample.

9. A device for measuring the acoustic properties and their changes according to claim 8 wherein said produced DC voltage is integrated before it is added to said FM signal.

10. A device for measuring the acoustic properties and their changes according to claim 9 including means for measuring the amplitude of said integrated DC voltage to give an indication of the shift in the frequency of the mechanical resonant peak in said sample.

* * * * *